(12) United States Patent
Ahn et al.

(10) Patent No.: US 9,757,356 B2
(45) Date of Patent: Sep. 12, 2017

(54) COMPOSITION COMPRISING BIO COMPOUND FOR TREATING CARDIOVASCULAR DISEASE

(71) Applicant: CHONNAM NATIONAL UNIVERSITY HOSPITAL, Gwangju (KR)

(72) Inventors: Youngkeun Ahn, Gwangju (KR); Yong Sook Kim, Gwangju (KR); Hye-yun Jeong, Gwangju (KR); Darren R. Williams, Gwangju (KR); Da-Woon Jung, Gwangju (KR)

(73) Assignee: CHONNAM NATIONAL UNIVERSITY HOSPITAL, Gwangju (KR)

( * ) Notice: Subject to any disclaimer, the term of this patent is extended or adjusted under 35 U.S.C. 154(b) by 0 days.

(21) Appl. No.: 15/223,159

(22) Filed: Jul. 29, 2016

(65) Prior Publication Data

US 2017/0100372 A1    Apr. 13, 2017

(30) Foreign Application Priority Data

Oct. 12, 2015  (KR) .......................... 10-2015-0142343

(51) Int. Cl.
*A61K 31/404*    (2006.01)

(52) U.S. Cl.
CPC .................. *A61K 31/404* (2013.01)

(58) Field of Classification Search
None
See application file for complete search history.

(56) References Cited

FOREIGN PATENT DOCUMENTS

KR    101290509 B1    7/2013

OTHER PUBLICATIONS

K. A. Bicknell, et al; Reprogramming the cell cycle machinery to treat . . . ; Current opinion in pharmacology; Science Direct; 2008, vol. 8, pp. 193-201.
A. S. Tseng, et al; The GSK-3 Inhibitor BIO Promotes Proliferation . . . ; Chemistry & biology; 2006, vol. 13, pp. 957-963.
Yong Sook Kim et al. "GSK-3 inhibitor BIO ameliorates cardiac fibrosis and dysfunction after myocardial infarction through selective inhibition of fibroblast proliferation" Abstract from Oral Presentation, 58th Annual Scientific Meeting of The Korean Society of Cardiology; Nov. 28, 2014.

*Primary Examiner* — Brian J Davis
(74) *Attorney, Agent, or Firm* — Lucas & Mercanti, LLP

(57) ABSTRACT

A pharmaceutical composition and a method for preventing or treating a cardiovascular disease are provided. The pharmaceutical composition includes a BIO compound ((2'Z, 3'E)-6-bromoindirubin-3'-oxime) or a pharmaceutically acceptable salt thereof as an active ingredient. The pharmaceutical composition can specifically act on different types of cells constituting heart tissues, that is, can induce the growth of cardiomyocytes, and can also inhibit proliferation of cardiac fibroblasts and strongly suppress inflammatory mediators in macrophages, thereby significantly recovering the tissues and functions of the heart after the onset of myocardial infarction. Therefore, the pharmaceutical composition can be effectively used to treat various cardiovascular diseases including myocardial infarction.

6 Claims, 8 Drawing Sheets

COMPOSITION COMPRISING BIO COMPOUND FOR TREATING CARDIOVASCULAR DISEASE

CROSS-REFERENCE TO RELATED APPLICATION

This application claims priority to and the benefit of Korean Patent Application No. 2015-0142343, filed on Oct. 12, 2015, the disclosure of which is incorporated herein by reference in its entirety.

The present invention was undertaken with the support of Developing a small molecule-based novel technology to induce cardiac cells No. 2015M3A9C6031684 grant funded by the Bio & Medical Technology Development Program of the NRF funded by the Korean government, and Developing NF-κB modulation-based cardiovascular therapeutics No. HI13C1527 grant funded by the Ministry of Health & Welfare (MW).

BACKGROUND

1. Field of the Invention

The present invention relates to a pharmaceutical composition and a method for preventing or treating a cardiovascular disease, the pharmaceutical composition including a (2'Z,3'E)-6-bromoindirubin-3'-oxime (BIO) compound or a pharmaceutically acceptable salt thereof as an active ingredient.

2. Discussion of Related Art

Myocardial infarction is a disease in which cardiac function declines due to apoptosis or necrosis of cardiomyocytes caused by shut off of the supply of oxygen and nutrients when blood flow is blocked due to main blood vessels of the heart being clogged. Since the apoptosis/necrosis of cardiomyocytes after myocardial infarction induces inflammation in tissues and causes a decline in contractile function of the heart muscle, as a compensatory mechanism, our bodies respond by promoting an inflow of macrophages to remove residual by-products of cardiomyocytes and inducing angiogenesis to resume the blood flow at the infarct sites. Also, to maintain the contractile function, cardiac fibroblasts proliferate and migrate to the infarct sites and then substitute for the sites where cardiomyocytes have been lost by forming an extracellular matrix. As a result, inflammatory responses in the heart tissues may be re-initiated, and a pump function of the heart may be declined.

It is known that the post-myocardial infarction death most frequently occurs within several hours of the onset of infarction, that is, approximately 50% of patients die within an hour, and approximately 80% of patients die within 24 hours. Therefore, early treatment of myocardial infarction is required, and the recurrence of the myocardial infarction needs to be prevented to reduce the long-term mortality and morbidity after the myocardial infarction.

As drugs for prevention and treatment of myocardial infarction, drugs such as aspirin, an antithrombotic drug, and the like have been known in the related art. However, aspirin has problems including allergy, drug tolerance, etc., and the antithrombotic drug has a risk of bleeding. Also, since the mortality surpasses 10% within one year after treatment of myocardial infarction and there are no other alternatives but to transplant a heart due to irreversible development into heart failure, a development of novel drugs having a potent therapeutic effect is needed.

Meanwhile, glycogen synthase kinase-3 (GSK-3) is a serine/threonine protein kinase that is composed of α and β isoforms encoded by separate genes and is known to be associated with a signaling pathway for regulating various cell functions. Since the abnormality in the pathway using GSK3 as a regulator is associated with the pathogenesis of diseases such as leukemia, diabetes, Alzheimer's disease, and neuropathy, an inhibitor targeting GSK3 to treat these diseases has been under an active development (Korean Registered Patent No. 10-1290509).

As a GSK3 inhibitor, a compound (2'Z,3'E)-6-bromoindirubin-3'-oxime (hereinafter referred to as a 'BIO' compound) is a compound that suppresses enzymatic activities of GSK3β which is an enzyme associated with glycogen metabolism and is reported to have effects on differentiation of stem cells, treatment of diabetes, and Alzheimer's disease. However, it remains to be revealed whether, in addition to proliferation of the cardiomyocytes, the functional/structural deterioration of infarct cardiac muscle may be improved under the control of pathological microenvironments, for example, improved by selectively inhibiting the proliferation of cardiac fibroblasts and suppressing an inflammatory phenotype of macrophages.

SUMMARY OF THE INVENTION

Accordingly, the present inventors have found that a BIO compound selectively acts on cardiomyocytes, cardiac fibroblasts, and inflammatory macrophages, all of which constitute the heart, after the onset of myocardial infarction to control pathological microenvironments in a cardiac muscle and thus can treat various cardiovascular diseases including myocardial infarction. Therefore, the present invention has been completed based on these facts.

Therefore, the present invention is directed to a pharmaceutical composition which includes a BIO compound as an active ingredient for preventing or treating a cardiovascular disease.

Also, the present invention is directed to providing a method of treating a cardiovascular disease using the pharmaceutical composition and the use of the pharmaceutical composition.

However, the problems to be solved according to the present invention are not limited to the above-described problems, and other problems which are not disclosed herein may be made apparent to those skilled in the art by the detailed description provided below.

According to an aspect of the present invention, there is provided a pharmaceutical composition which includes a BIO compound represented by the following Formula 1 or a pharmaceutically acceptable salt thereof as an active ingredient for preventing or treating a cardiovascular disease.

[Formula 1]

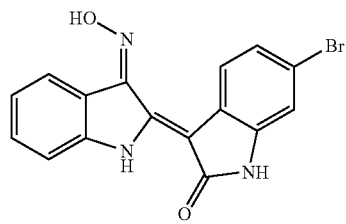

According to another aspect of the present invention, there is provided a method of preventing or treating a cardiovascular disease, which includes administering the BIO compound or the pharmaceutically acceptable salt thereof to a subject.

According to still another aspect of the present invention, there is provided a use of the BIO compound or the pharmaceutically acceptable salt thereof for preventing or treating a cardiovascular disease.

According to one exemplary embodiment of the present invention, the BIO compound may be included at a concentration of 2.5 to 5 µM.

According to another exemplary embodiment of the present invention, the prevention or treatment of the cardiovascular disease may be realized by promoting proliferation of cardiomyocytes and inhibiting proliferation of cardiac fibroblasts.

According to another exemplary embodiment of the present invention, the prevention or treatment of the cardiovascular disease may be realized by inhibiting inflammatory responses of macrophages.

According to yet another exemplary embodiment of the present invention, the cardiovascular disease may be myocardial infarction, angina, atherosclerosis, or arrhythmia.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
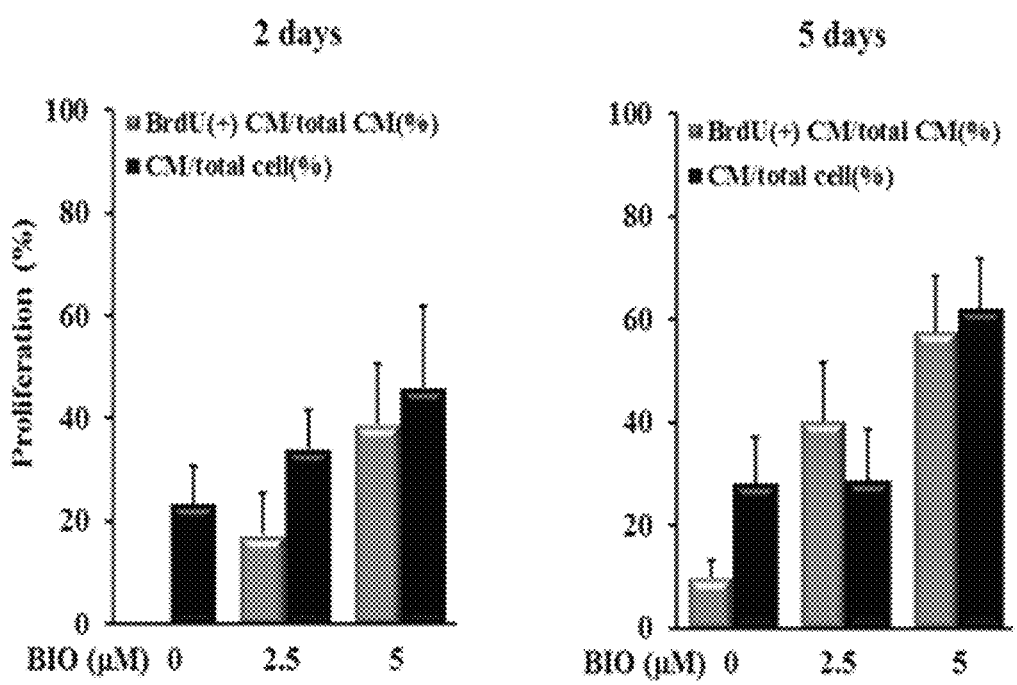
FIG. 1 shows results of confirming and quantifying an effect of a BIO compound on induction of proliferation of cardiomyocytes (CMs) using a BrdU-cell proliferation assay.

Exemplary embodiments of the present invention will be described in detail below with reference to the accompanying drawings. While the present invention is shown and described in connection with exemplary embodiments thereof, it will be apparent to those skilled in the art that various modifications can be made without departing from the scope of the invention.

Unless specifically stated otherwise, all the technical and scientific terms used in this specification have the same meanings as what are generally understood by a person skilled in the related art to which the present invention belongs. In general, the nomenclatures used in this specification and the experimental methods described below are widely known and generally used in the related art.

The present invention provides a pharmaceutical composition for preventing or treating a cardiovascular disease, which includes a compound represented by the following Formula 1 (a 'BIO' compound) or a pharmaceutically acceptable salt thereof as an active ingredient.

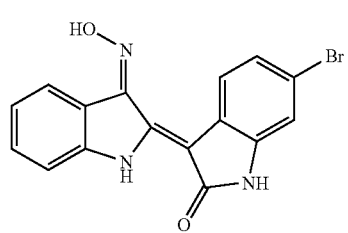 [SMILES: O=C1Nc2cc(Br)ccc2/C1=C1/Nc2ccccc2/C1=N\O]

[Formula 1]

The BIO compound ((2'Z,3'E)-6-bromoindirubin-3'-oxime) is known as a reversible ATP-competitive GSK-3β inhibitor and has been first reported as a substance that maintains embryonic stem cells in an undifferentiated state in human beings and mice. The pharmaceutical composition of the present invention includes such a BIO compound and derivatives thereof having the same/similar in vivo or in vitro effect.

In the composition according to one exemplary embodiment of the present invention, the BIO compound may be prepared using a pharmaceutically acceptable salt and a solvate thereof according to a conventional method known in the related art. Unless otherwise particularly specified, the 'pharmaceutically acceptable salt' includes a salt of an acidic or basic group. For example, the pharmaceutically acceptable salt may include sodium, calcium and potassium salts of a hydroxyl group, and other pharmaceutically acceptable salts of an amino group may include salts such as hydrobromide, sulfate, hydrogen sulfate, phosphate, hydrogen phosphate, dihydrogen phosphate, acetate, succinate, citrate, tartrate, lactate, mandelate, methane sulfonate (mesylate), and p-toluene sulfonate (tosylate). In this case, the pharmaceutically acceptable salt may be prepared using methods or procedures of preparing a salt as known in the related art.

In the composition according to one exemplary embodiment of the present invention, the BIO compound may be included at a concentration of 1 to 10 µM, preferably a concentration of 2.5 to 5 µM, and more preferably a concentration of 5 μM. Effects may not be expressed when the concentration is too low, whereas toxicity may be expressed when the concentration is too high. As a result, a proper concentration of the BIO compound should be checked depending on the situation.

In the present invention, the cardiovascular disease is not particularly limited but may preferably include cardiovascular diseases including myocardial infarction, angina, atherosclerosis, arrhythmia, etc. Also, the treatment of the cardiovascular disease encompasses a meaning that includes relieving and alleviating a cardiovascular disease and improving symptoms of the cardiovascular disease and also lowering the probability of developing the cardiovascular disease.

The pharmaceutical composition according to one exemplary embodiment of the present invention may further include components including a conventional therapeutically active ingredient, other adjuvants, a pharmaceutically acceptable carrier, etc. In this case, the pharmaceutically acceptable carrier is generally used during preparations and includes saline, sterile water, a Ringer's solution, buffered saline, cyclodextrin, a dextrose solution, a maltodextrin solution, glycerol, ethanol, a liposome, etc., but the present invention is not limited thereto. When necessary, the pharmaceutical composition may further include other typical additives including an antioxidant, a buffer, and the like. Also, a diluent, a dispersant, a surfactant, a binder, glucosyl cyclodextrin, and the like may be further added into the composition which, then, may be formulated into injectable formulations including an aqueous solution, a suspension, an emulsion, etc., pills, capsules, granules, or tablets. For the proper pharmaceutically acceptable carriers and the formulations, the composition may preferably be formulated according to each component using a method such as one disclosed in Remington's Pharmaceutical Science (Mack Publishing Company, Easton Pa.). The pharmaceutical composition according to one exemplary embodiment of the present invention may be formulated into injections, inhalations, or external preparations for skin, but the present invention is not limited thereto.

In the present invention, the term 'subject' refers to a target in need of a treatment for a disease and, more particularly, to a mammal including a human or a non-human primate, a mouse, a rat, a dog, a cat, a horse, cattle, etc.

In the present invention, the 'pharmaceutically effective amount' may be determined according to factors including the type and severity of a disease to be treated, the age and sex of a patient, the sensitivity to a drug, an administration time, a route of administration, an excretion rate, a therapeutic period, drugs to be used together, and other factors widely known in the pharmaceutical field. In this case, the pharmaceutically effective amount is an amount that may be determined in consideration of all the factors to obtain the maximum effect without any side effects and thus may be easily determined by those skilled in the art.

The 'administration method' may be used without limitation as long as the composition according to one exemplary embodiment of the present invention can reach target tissues. For example, the administration method' encompasses oral administration, intraarterial injection, intravenous injection, percutaneous injection, intranasal administration, transbronchial administration, or intramuscular administration. The composition may be administered daily at a dose of approximately 0.0001 to 100 mg/kg, preferably 0.001 to 10 mg/kg, and may be administered once a day or multiple times in divided doses.

The composition according to one exemplary embodiment of the present invention may be widely used in drugs, foods, and drinks to prevent and improve a cardiovascular disease and may be used in the form of a powder, granules, a pill, a capsule, or a beverage.

In the present invention, it was found that the BIO compound induces the proliferation of cardiomyocytes (CMs) but inhibits the proliferation of cardiac fibroblasts (cFBs). Therefore, it was confirmed that, among the cardiomyocytes and cardiac fibroblasts coexisting in the heart tissues, the BIO compound selectively activates the cardiomyocytes acting positively for a recovery of the cardiac functions after the onset of myocardial infarction and selectively deactivates the cardiac fibroblasts acting negatively for a recovery of the cardiac functions (Examples 2 to 4).

Also, in the present invention, it was confirmed that the BIO compound is effective in actually satisfactorily maintaining the diastolic and systolic functions of the heart in an MI animal model to improve the cardiac functions and suppressing myocardial fibrosis to treat myocardial infarction (Example 5).

In addition, in the present invention, it was confirmed that the BIO compound is effective in inhibiting the inflammatory characteristics of macrophages in vitro (in a macrophage cell line) and in vivo (an MI animal model) to treat myocardial infarction (Example 6).

Further, in the present invention, it was confirmed that a selective effect of the BIO compound on the proliferation of the cardiomyocytes and cardiac fibroblasts is not associated with the GSK3β inhibitory activities, and, when the inhibitory effect on the proliferation of the cardiac fibroblasts was compared to that of another GSK3β inhibitor (LiCl), it was confirmed that the inhibitory effect is a distinctive nature of the BIO compound not observed for LiCl (Example 7).

Hereinafter, preferred Examples are provided to aid in understanding the present invention. However, it should be understood that detailed description provided herein is merely intended to provide a better understanding of the present invention and is not intended to limit the scope of the present invention.

EXAMPLES

Example 1: Preparation of Samples and Cell Culture 1-1. Preparation of Samples

For use in a cell experiment, a BIO compound (Sigma) was dissolved in DMSO and diluted with a cell culture broth. For use in an animal experiment, the BIO compound (Sigma) was dissolved in a solution in which phosphate-buffered saline (PBS) and ethyl alcohol were mixed at a ratio of 1:1 and intraperitoneally injected daily into laboratory rats at a dose of 0.2 kg/body weight.

1-2. Heart Cell Culture

Hearts of two-day-old rats were removed and washed with physiological saline. Thereafter, left cardiac muscles were separated from the hearts in a sterilization cabinet, and microtomed into segments. These myocardial tissues were added to a collagenase enzyme solution, reacted at 37° C. while stirring, and then centrifuged to collect only the supernatant which were then kept in a cell culture flask. After an hour, cardiomyocytes which floated when the supernatant was transferred to a new culture flask were separated from cardiac fibroblasts attached to the bottom of the cell culture flask. At this point, both the cardiomyocytes and the cardiac fibroblasts were cultured in a Dulbecco's modified Eagle's medium (DMEM) supplemented with 10% fetal bovine serum (FBS) and then used for experiments.

Example 2: Effect of BIO Compound on Induction of Proliferation of Cardiomyocytes (CMs)

To examine the effect of the BIO compound on the proliferation of heart cells, cardiomyocytes (CMs) and cardiac fibroblasts (cFbs) were co-cultured and were treated with BIO at concentrations of 2.5 µM and 5 µM, respectively. After 2 days and 5 days, the proliferation of cells was quantified.

Since the cardiomyocytes and the cardiac fibroblasts co-exist in the heart tissues after the onset of myocardial infarction, a co-culture model was used to simulate the cardiomyocytes and the cardiac fibroblasts. The cardiomyocytes were detected using an antibody against a cardiomyocyte-specific protein referred to as cardiac troponin I to distinguish the cardiomyocytes from the cardiac fibroblasts.

To determine the level of new DNA synthesis, a cell proliferation assay was performed by adding bromodeoxyuridine (BrdU) to a cell culture broth in advance to incorporate BrdU into DNAs of cells and performing a chromogenic reaction using an anti-BrdU antibody.

As a result, it could be seen that both the 'BrdU (+) CM/total CM' (grey bars) representing a proliferation rate of dividing (proliferating) cardiomyocytes among the cardiomyocytes which were under culture; and the 'CM/total cell' (black bars) representing a ratio of the cardiomyocytes among both the cardiomyocytes and cardiac fibroblasts which were under culture significantly increased by the treatment of BIO, as shown in FIG. 1. In this case, the BrdU (+) cells represent cells which are under proliferation, the total cells represent the cardiomyocytes and cardiac fibroblasts which are under culture, and the total CM represent the cardiomyocytes which are under culture.

Example 3: Inhibitory Effect of BIO on Proliferation of Cardiac Fibroblasts (cFBs)

To examine an inhibitory effect of the BIO compound on the proliferation of cardiac fibroblasts (cFBs) in the cardiomyocyte/cardiac fibroblast co-culture model used in Example 2, the total cells were stained with 4',6-Diamidino-2-phenylindole dihydrochloride (DAPI) and counted. Then, cells which were not stained with cardiac troponin I but stained with DAPI were regarded as cardiac fibroblasts and then counted.

Figure 2:
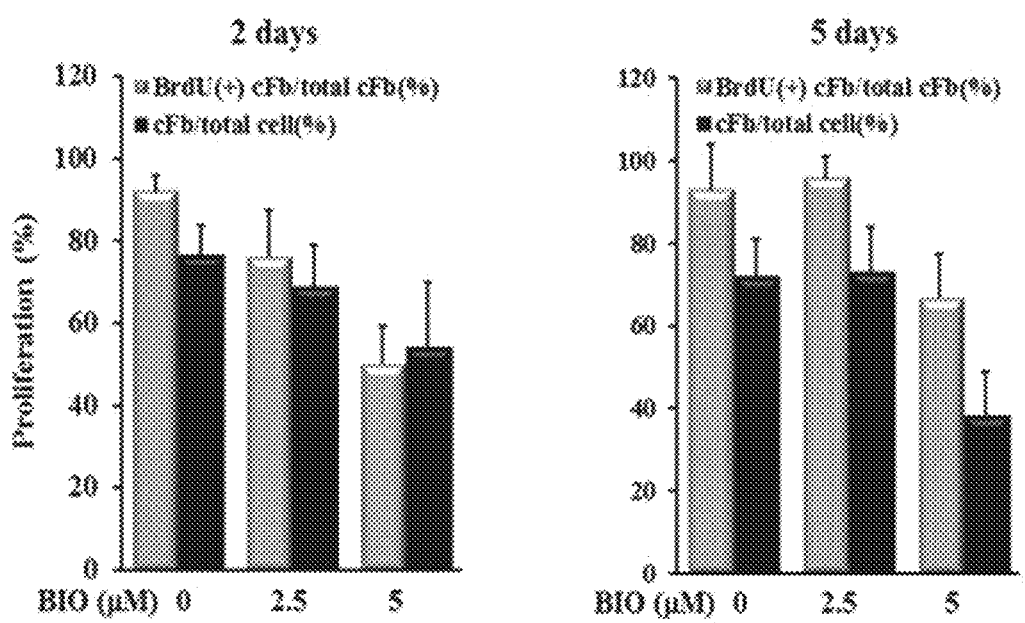
FIG. 2 shows results of confirming and quantifying an effect of the BIO compound on inhibition of proliferation of cardiac fibroblasts (cFBs) using a BrdU-cell proliferation assay.

As a result, it could be seen that both the 'BrdU (+) cFB/total cFB' (grey bars) representing a proliferation rate of dividing (proliferating) cardiac fibroblasts among the cardiac fibroblasts which were under culture; and the 'cFB/total cell' (black bars) representing a ratio of the cardiac fibroblasts among both the cardiomyocytes and cardiac fibroblasts which were under culture significantly decreased by the treatment of BIO, as shown in FIG. 2.

Example 4: Effect of BIO on Selective Regulation of Cardiomyocytes and Cardiac Fibroblasts To evaluate whether the cardiomyocytes and cardiac fibroblasts are selectively regulated by BIO, only the cell proliferation rate obtained by the treatment of 5 µM BIO from the results obtained in Examples 2 and 3 was calculated and quantified.

Figure 3:
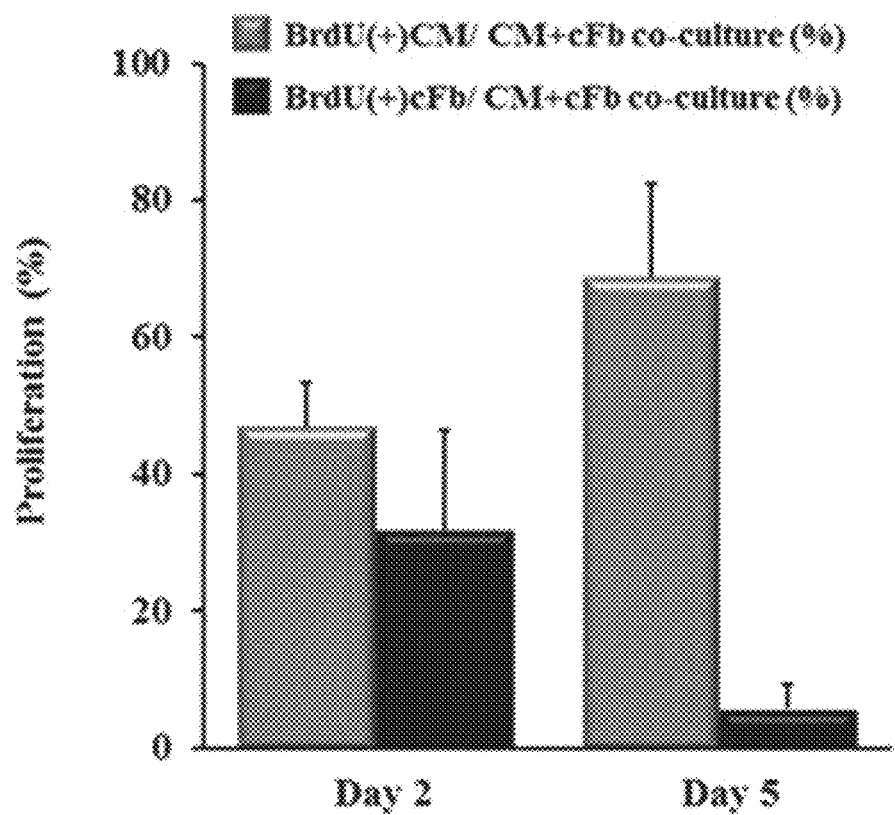
FIG. 3 shows results of calculating and quantifying only the cell proliferation rate when cells are treated with BIO (5 µM) to evaluate an effect of the BIO compound on selective regulation of the cardiomyocytes and cardiac fibroblasts.

As a result, it could be seen that the proliferation of the cardiomyocytes (grey bars) and cardiac fibroblasts (black bars) were reversely, that is, selectively regulated by BIO, as shown in FIG. 3.

Example 5: Effect of BIO on Improvement of Cardiac Function/Myocardial Fibrosis after Myocardial Infarction To determine whether the BIO compound actually improves the cardiac functions and suppresses myocardial fibrosis in an MI animal model, an experiment was performed as follows.

To induce the onset of myocardial infarction, first of all, rats weighing 200 to 230 g were anesthetized with ketamine (50 mg/kg) and xylazine (5 mg/kg), and the chests of the rats were shaved and disinfected. An anesthesia ventilator was installed to manage the airway of the rat, and the chest was incised to expose the heart. Then, a cardiac muscle was sutured in a region of the left anterior descending artery (LAD) to block a blood flow, thereby establishing an MI animal model.

Thereafter, physiological saline or BIO was intra-abdominally injected daily to the rats at a dose of 0.2 mg/body weight in the MI animal model. After two weeks, the rats were anesthetized, and subjected to echocardiography to examine the cardiac functions. As a result, it could be seen the diastolic and systolic functions of the heart were well preserved in the BIO-treated group (MI+BIO), compared to the control (MI+saline), as listed in the following Table 1 (*; there is a statistical difference between the BIO-treated group and the physiological saline-treated group).

TABLE 1

| Index | Non-MI | MI + Saline | MI + BIO |
|---|---|---|---|
| IVSd | 0.110 ± 0.029 | 0.063 ± 0.013 | 0.079 ± 0.013* |
| IVSs | 0.140 ± 0.022 | 0.070 ± 0.014 | 0.084 ± 0.028 |
| LVIDd | 0.893 ± 0.022 | 1.013 ± 0.026 | 0.900 ± 0.066* |
| LVIDs | 0.580 ± 0.012 | 0.885 ± 0.024 | 0.736 ± 0.074* |
| LVPWd | 0.130 ± 0.014 | 0.078 ± 0.010 | 0.089 ± 0.023 |
| LVPWs | 0.170 ± 0.012 | 0.073 ± 0.005 | 0.115 ± 0.019* |
| EDV | 1.523 ± 0.111 | 2.135 ± 0.153 | 1.563 ± 0.308* |
| ESV | 0.460 ± 0.035 | 1.483 ± 0.121 | 0.911 ± 0.251* |
| EF | 69.845 ± 2.360 | 30.673 ± 1.659 | 41.313 ± 6.823* |
| SV | 1.063 ± 0.102 | 0.653 ± 0.052 | 0.651 ± 0.116 |
| FS | 35.180 ± 1.89 | 12.615 ± 0.755 | 18.262 ± 3.525* |

Figure 4:
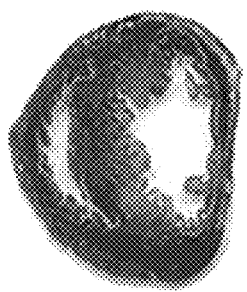
FIG. 4 shows results of determining whether the BIO compound suppresses myocardial fibrosis in a myocardial infarction (MI) animal model using a tissue staining method.
Figure 4:
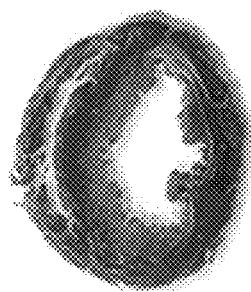
Figure 4:
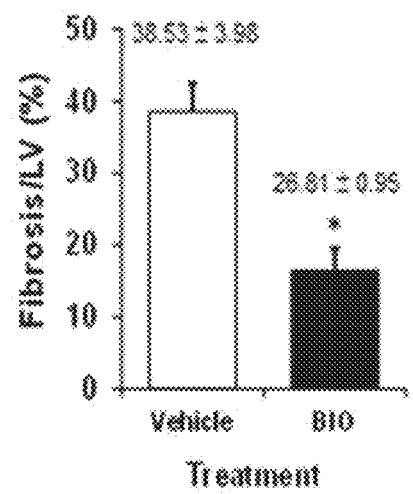

In this case, the indices have the following meanings.
IVSd; thickness of interventricular septum (diastole)
IVSs; thickness of interventricular septum (systole)
LVIDd; thickness of left ventricular internal dimension (diastole)
LVIDs; thickness of left ventricular internal dimension (systole)
LVPWd; left ventricle posterior wall thickness (diastole)
LVPWs; left ventricle posterior wall thickness (systole)
EF; ejection fraction
FS; fractional shortening To quantify myocardial fibrosis, the heart tissues were also removed, fixed with formalin, embedded in a paraffin block, and then microtomed into sections having a thickness of 10 µm. Thereafter, the sections were histologically stained using a Masson's trichrom method. As a result, it could be seen that fibrosis regions (blue) were significantly reduced in the BIO-treated group (MI+BIO), compared to the control (MI+vehicle), as shown in FIG. 4.

Example 6: Effect of BIO on Inhibition of Inflammatory Responses of Macrophages

6-1. Confirmation of In Vitro Inhibitory Effect

A mouse macrophage cell line RAW264.7 (Korean Cell Line Bank) was cultured in a DMEM broth supplemented with 10% fetal bovine serum, and lipopolysaccharide (LPS) was added at a concentration of 100 ng/mL to the culture broth to initiate inflammation of macrophages. Thereafter, the culture cells were treated with the BIO compound at concentrations of 0, 1, 2.5, and 5 µM, and an effect of the BIO compound on induction of expression of an inducible nitric oxide synthase (iNOS) as an inflammatory marker was confirmed using Western blotting.

Figure 5:
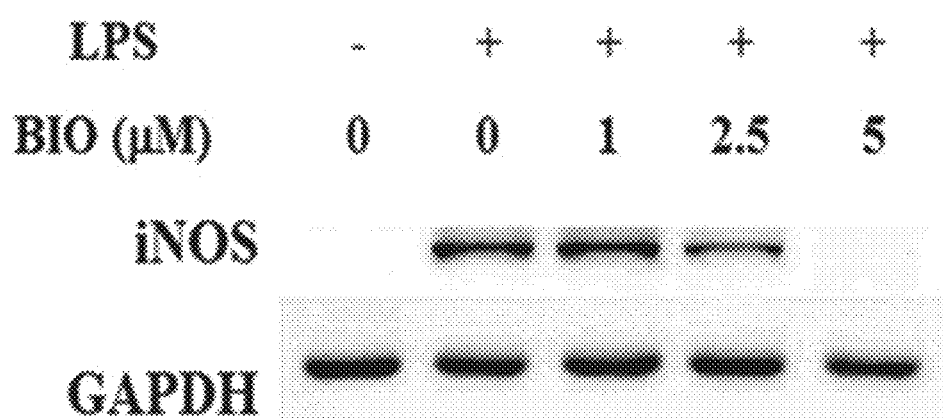
FIG. 5 shows results of determining whether or not an expression level of an inflammatory marker (iNOS) in a macrophage cell line (RAW264.7) is reduced using a Western blotting assay to evaluate an effect of the BIO compound on in vitro inhibition of inflammatory responses of the macrophages.

As a result, it could be seen that the expression of iNOS was lowered in a concentration-dependent manner in the BIO-treated group compared to the BIO-untreated group, as shown in FIG. 5, indicating that the inflammatory responses of the macrophage were suppressed by the BIO compound.

6-2. Confirmation of In Vivo Inhibitory Effect

Macrophages may be mainly divided into an inflammatory M1 type and an anti-inflammatory M2 type. At the beginning of inflammation in the tissues, the macrophages function to remove a surrounding infection source such as impurities or bacteria due to the inflammatory M1 characteristics and then are converted into anti-inflammatory M2 characteristics to terminate an inflammatory response in the tissues and restore damaged tissues. However, when such normal responses do not occur, morbid inflammation lasts, and a healing process of the tissues is delayed, resulting in degraded structure and functions of the heart.

Therefore, to evaluate the effect the BIO compound had on such changes in the characteristics of the macrophages in the MI animal model, the characteristics of the macrophages flowing from the heart tissues into the cardiac muscle in the MI animal model used in Example 5 were confirmed using an immunofluorescence staining method.

Specifically, a slide for myocardial infarction heart tissues was treated with an anti-CD68 antibody and an anti-Arg1 antibody, and a fluorescence image was visualized using a secondary antibody. Then, the tissues were observed under a confocal microscope with a magnification of 800 times. Since the macrophages in the tissues expressed CD68, the macrophages were detected using the anti-CD68 antibody. Also, since a marker used to distinguish the characteristics of the macrophages in the tissues was iNOS in the case of the inflammatory M1 macrophages and arginase 1 (Arg1) in the case of the anti-inflammatory M2 macrophages, the macrophages were stained with an anti-inflammatory marker Arg1 for macrophages in order to determine how many the phenotype of the macrophages in the heart was converted into the M2 type at the $2^{nd}$ week after the onset of myocardial infarction.

Figure 6:
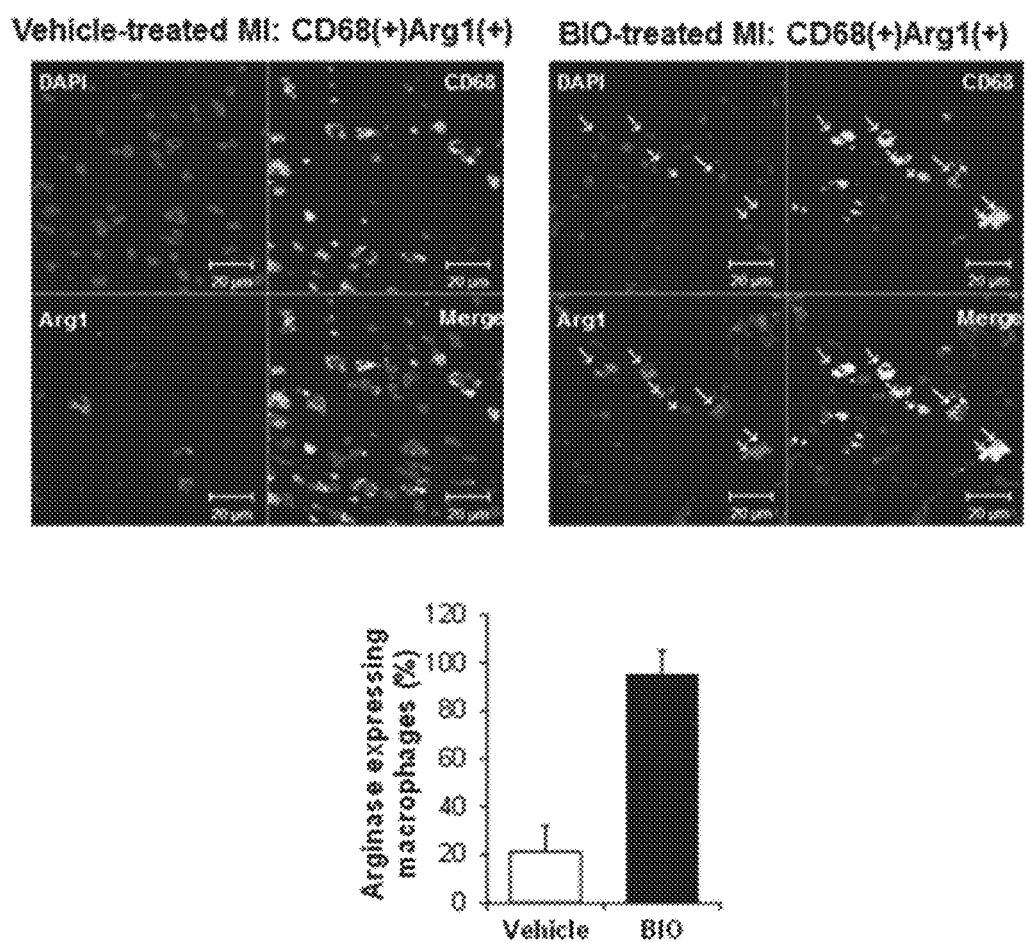
FIG. 6 shows results of determining characteristics of macrophages flowing in cardiac muscle in the MI animal model using an immunofluorescence staining method to evaluate an effect of the BIO compound on in vitro inhibition of inflammatory responses of the macrophages.

As a result, it could be seen that the Arg1-expressing macrophages prevailed in the cardiac muscles in the BIO-treated group, indicating that the BIO compound induced the changes in the characteristics of the macrophages into the anti-inflammatory M2 type in the MI animal model, as shown in FIG. 6.

Example 7: Experiment for Comparison of BIO with Nanother GSK3 Inhibitor (LiC1)

7-1. GSK3β Inhibition

To determine whether the selective effect of the BIO compound on the proliferation of the cardiomyocytes and cardiac fibroblasts was associated with the GSK3β inhibitory activity, an experiment for a comparison with LiCl known as another GSK3β inhibitor was performed. Since GSK3β was in an inert state when phosphorylated, an increase in expression level of p-GSK3β was determined using Western blotting in order to evaluate the inhibition of GSK3β.

Specifically, cardiac fibroblasts were treated with the BIO compound and LiCl at concentrations of 0, 0.25, 2.5, and 5 µM for 2 days, and then subjected to Western blotting using anti-p-GSK3β and anti-GSK3β antibodies.

Figure 7:
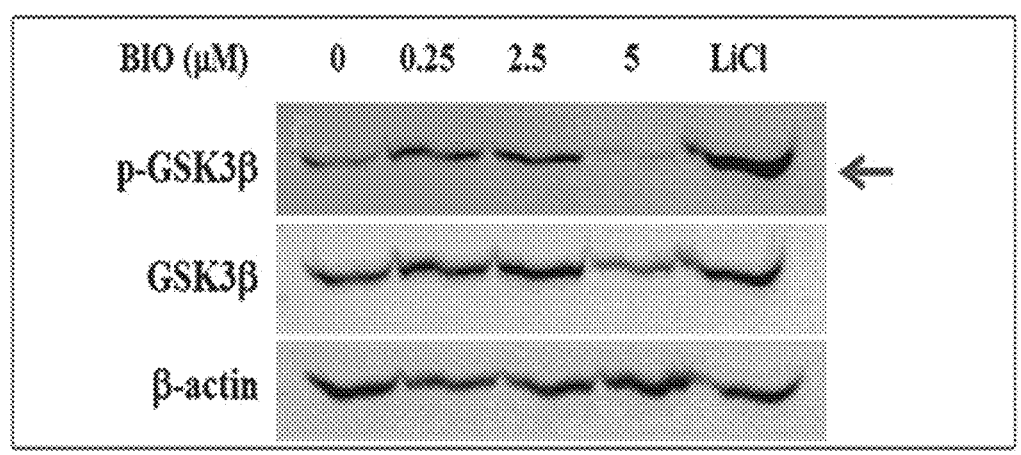
FIG. 7 shows results of treating cardiac fibroblasts with each of the BIO compound and another GSK3β inhibitor (LiCl) and comparatively evaluating an expression level of p-GSK3β (inactive) using a Western blotting method to determine whether a selective effect of the BIO compound on proliferation of the cardiomyocytes and cardiac fibroblasts is associated with the GSK3β inhibitory activity.

As a result, it was revealed that an expression level of p-GSK3β in an inert form increased only when the cardiac fibroblasts were treated with LiCl in the LiCl-treated group, compared to the BIO (5 µM)-treated group, as shown in FIG. 7. Although BIO is known as a GSK3β inhibitor in the art, according to the present invention, such results show that BIO did not exhibit the inhibitory activity of GSK3β in the cardiac fibroblasts.

7-2. Inhibition of Proliferation of Cardiac Fibroblasts

An inhibitory effect on the proliferation of the cardiac fibroblasts was comparatively evaluated in the same manner as in Example 3 in the BIO-treated group and the LiCl-treated group.

Figure 8:
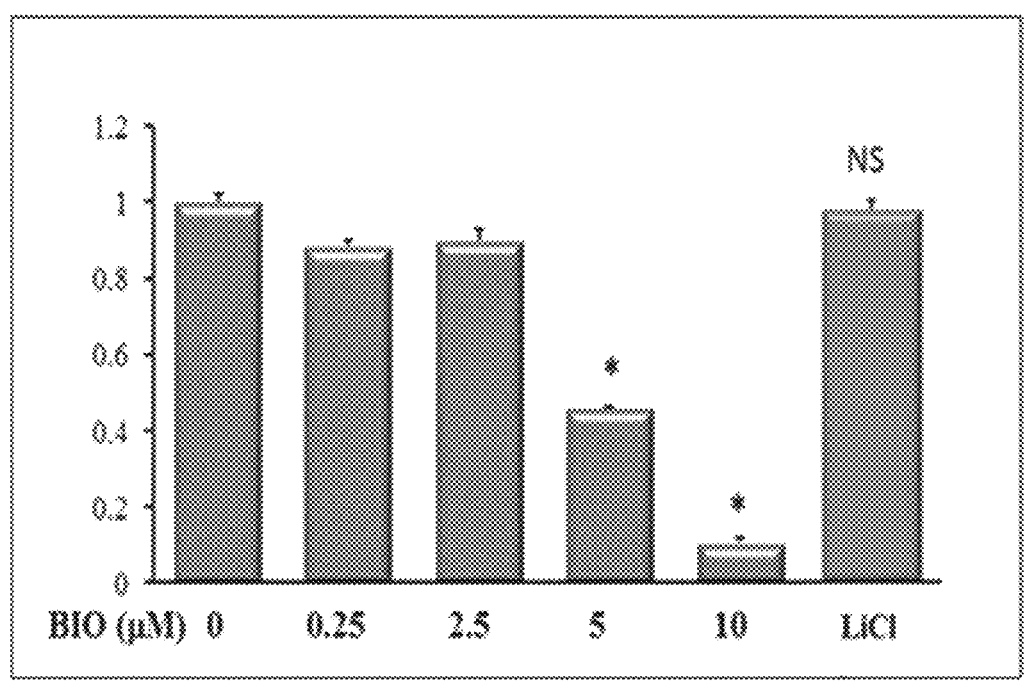
FIG. 8 shows results of comparatively evaluating an inhibitory effect on the proliferation of the cardiac fibroblasts in a BIO-treated group and a group treated with another GSK3β inhibitor (LiCl).

As a result, it was revealed that the inhibitory effect on the proliferation of the cardiac fibroblasts was observed only in the BIO (5 µM and 10 µM)-treated groups and was not observed in the LiCl-treated group, as shown in FIG. 8. Such results suggested that the BIO compound selectively inhibited the proliferation of the cardiac fibroblasts by means of an action mechanism distinct from the inhibitory activity of the GSK3β enzyme.

The pharmaceutical composition including the BIO compound according to one exemplary embodiment of the present invention can specifically act on different types of cells constituting heart tissues, that is, can induce the growth of cardiomyocytes and can also inhibit proliferation of cardiac fibroblasts and strongly suppress inflammatory mediators in macrophages, thereby significantly recovering the tissues and functions of the heart after the onset of myocardial infarction. Therefore, the pharmaceutical composition can be effectively used to treat various cardiovascular diseases including myocardial infarction.

Also, according to the present invention, since a single compound referred to as the BIO compound differently acts on different types of cells constituting the heart tissues to have a myocardial protective effect, the pharmaceutical composition will be expected to have a therapeutic effect on other diseases accompanied by inflammation or pathological fibrosis.

It will be apparent to those skilled in the art that various modifications can be made to the above-described exemplary embodiments of the present invention without departing from the scope of the invention. Thus, it is intended that the present invention covers all such modifications provided they come within the scope of the appended claims and their equivalents.

What is claimed is:

1. A method of treating a cardiovascular disease, comprising inhibiting proliferation of cardiac fibroblasts in vivo by administering a compound represented by the following Formula 1 or a pharmaceutically acceptable salt thereof to a subject

[Formula 1]

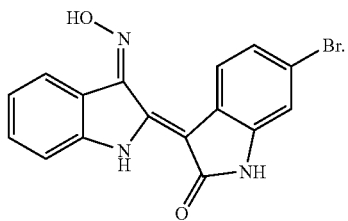

2. The method of claim 1, wherein the compound is included at a concentration of 2.5 to 5 μM.

3. The method of claim 1, wherein the cardiovascular disease is myocardial infarction, angina, atherosclerosis, or arrhythmia.

4. A method of treating a cardiovascular disease, comprising inhibiting inflammatory responses of macrophages in vivo by administering a compound represented by the following Formula 1 or a pharmaceutically acceptable salt thereof to a subject

[Formula 1]

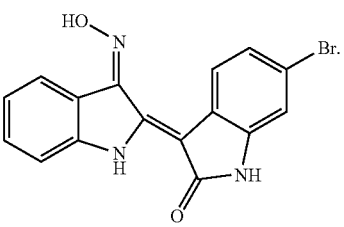

5. The method of claim 1, wherein the compound is included at a concentration of 2.5 to 5 μM.

6. The method of claim 1, wherein the cardiovascular disease is myocardial infarction, angina, atherosclerosis, or arrhythmia.

* * * * *